(12) United States Patent
Simpson et al.

(10) Patent No.: US 8,658,408 B2
(45) Date of Patent: Feb. 25, 2014

(54) PROCESS FOR PRODUCTION OF ALCOHOLS BY MICROBIAL FERMENTATION

(71) Applicant: LanzaTech New Zealand Limited, Roselle, IL (US)

(72) Inventors: Sean Dennis Simpson, Auckland (NZ); Loan Phuong Tran, Auckland (NZ); Christophe Daniel Mihalcea, Auckland (NZ); Jennifer Mon Yee Fung, Auckland (NZ); FungMin Liew, Auckland (NZ); Shane Fleming, Auckland (NZ)

(73) Assignee: Lanza Tech New Zealand Limited, Auckland (NZ)

( * ) Notice: Subject to any disclaimer, the term of this patent is extended or adjusted under 35 U.S.C. 154(b) by 0 days.

(21) Appl. No.: 13/777,806

(22) Filed: Feb. 26, 2013

(65) Prior Publication Data

US 2013/0177955 A1  Jul. 11, 2013

Related U.S. Application Data (63) Continuation-in-part of application No. 12/997,063, filed as application No. PCT/NZ2009/000101 on Jun. 5, 2009, now abandoned.

(60) Provisional application No. 61/060,113, filed on Jun. 9, 2008.

(51) Int. Cl.
    *C12P 5/00*    (2006.01)

(52) U.S. Cl.
    USPC .......................................... 435/166; 435/170

(58) Field of Classification Search
    None
    See application file for complete search history.

(56) References Cited

U.S. PATENT DOCUMENTS

| | | | |
|---|---|---|---|
| 4,539,293 | A | 9/1985 | Bergstrom et al. |
| 4,851,344 | A | 7/1989 | Simon et al. |
| 5,173,429 | A | 12/1992 | Gaddy et al. |
| 5,593,886 | A | 1/1997 | Gaddy |
| 5,807,722 | A | 9/1998 | Gaddy |
| 5,821,111 | A | 10/1998 | Grady |
| 6,136,577 | A | 10/2000 | Gaddy |
| 6,340,581 | B1 | 1/2002 | Gaddy |
| 6,368,819 | B1 | 4/2002 | Gaddy et al. |
| 6,753,170 | B2 | 6/2004 | Gaddy et al. |
| 6,818,426 | B2 | 11/2004 | Yamamoto et al. |
| RE39,175 | E | 7/2006 | Gaddy et al. |
| 7,196,218 | B2 | 3/2007 | Gaddy et al. |
| 7,285,402 | B2 | 10/2007 | Gaddy et al. |
| 2005/0003500 | A1 | 1/2005 | Kudoh et al. |
| 2007/0259411 | A1* | 11/2007 | Bramucci et al. ............ 435/160 |
| 2007/0275447 | A1 | 11/2007 | Lewis et al. |
| 2009/0203100 | A1* | 8/2009 | Simpson et al. ............ 435/161 |
| 2010/0311104 | A1* | 12/2010 | Simpson et al. ............ 435/29 |
| 2010/0323417 | A1 | 12/2010 | Simpson et al. |

FOREIGN PATENT DOCUMENTS

| | | |
|---|---|---|
| CN | 1570123 | 1/2005 |
| CN | 1246465 | 3/2006 |
| CN | 1884560 | 12/2006 |
| CN | 11085996 | 12/2007 |
| DE | 4017113 | 12/1991 |
| EP | 0162771 | 11/1985 |
| EP | 1262550 | 12/2002 |
| EP | 18976557 A1 | 3/2008 |
| FR | 2574784 | 6/1986 |
| GB | 1493154 | 11/1977 |
| IN | 0190544 | 9/2003 |
| JP | 53068709 | 6/1978 |
| JP | 59020238 | 2/1984 |
| JP | 10234390 | 9/1989 |
| WO | 2006133637 | 12/2006 |
| WO | 2009058028 | 5/2007 |
| WO | 2007117157 | 10/2007 |
| WO | 2007130518 | 11/2007 |
| WO | 2007130521 | 11/2007 |
| WO | 2008028055 | 3/2008 |
| WO | 2008098254 | 8/2008 |
| WO | 2008101012 | 8/2008 |
| WO | 2008154301 | 12/2008 |
| WO | 2009020747 | 2/2009 |
| WO | WO2009094485 | 7/2009 |

OTHER PUBLICATIONS

Phillips, J.R., et al. "Synthesis gas a substrate for the biological production of fuels and chemicals." Applied Biochemistry and Biotechnology, 1994, 45/46. pp. 145-157.

Ragsdale, S.W. "Life with carbon monoxide." Critical Reviews in Biochemistry and Molecuiar Biology, 2004, 39, pp. 165-195.

Syu, M.-J. "Biological Production of 2,3-Butanediol" Applied Microbiology and Biotechnology 2001, vol. 55, pp. 10-18.

Henstra, et al. "Microbiology of Synthesis Gas Fermentation for Biofuel Production." Current Opinion in Biotechnology, 2007, 18, pp. 200-206.

(Continued)

*Primary Examiner* — Allison Ford
*Assistant Examiner* — Yvonne Pyla
(74) *Attorney, Agent, or Firm* — Frank S Molinaro (57) ABSTRACT

The invention provides method for producing butanediol and specifically 2,3-butanediol by anaerobic fermentation of a gaseous substrate comprising CO by a culture of at least one micro-organism. In accordance with particular methods of the invention, 2,3-butanediol is produced by anaerobic fermentation of substrates including carbohydrates and carbon monoxide. The invention further provides for the up-regulation of a native 2,3-butanediol dehydrogenase gene in the at least one micro-organism. The 2,3-butanediol can be further converted to compounds such as butene(s), butadiene and methyl ethyl ketone. These compounds can be further converted to chemical products such as 2-butanol.

21 Claims, 1 Drawing Sheet

(56) References Cited

OTHER PUBLICATIONS

Abrini, J. et al., *Clostridium autoethanogenum*, sp. nov., an Anaerobic Bacterium that Produces Ethanol from Carbon Monoxide, Archives of Microbiology, 1994, vol. 161, pp. 345-351.

Wardwell, S.A. et al., Expression of the *Klebsiella pneumoniae* CG21 Acetoin Reductase Gene in *Clostridium acetobutylicum* ATCC 824, Journal of Industrial Microbiology and Biotechnology, 2001, vol. 27, pp. 220-227.

* cited by examiner

PROCESS FOR PRODUCTION OF ALCOHOLS BY MICROBIAL FERMENTATION

CROSS REFERENCE TO RELATED APPLICATIONS

This application is a continuation-in-part of copending U.S. Ser. No. 12/997,063 filed on Mar. 7, 2011 which in turn is a National Stage filing of International Application No. PCT/NZ2009/000101 filed on Jun. 5, 2009 which claims priority to U.S. Provisional Application No. 61/060,113 filed on Jun. 9, 2008. The contents of all of said applications are incorporated by reference in their entirety.

FIELD OF THE INVENTION

The present invention relates to the production of butanediol by microbial fermentation, particularly to production of 2,3-butanediol by microbial fermentation of gaseous substrates comprising CO.

BACKGROUND

Biofuels for transportation are attractive replacements for gasoline and are rapidly penetrating fuel markets as low concentration blends. Biofuels, derived from natural plant sources, are more environmentally sustainable than those derived from fossil resources (such as gasoline), their use allowing a reduction in the levels of so-called fossil carbon dioxide ($CO_2$) gas that is released into the atmosphere as a result of fuel combustion. In addition, biofuels can be produced locally in many geographies, and can act to reduce dependence on imported fossil energy resources. Alcohols suitable for use as biofuels include ethanol, butanol and 2,3-butanediol.

Ethanol is rapidly becoming a major hydrogen-rich liquid transport fuel around the world. Worldwide consumption of ethanol in 2002 was an estimated 10.8 billion gallons. The global market for the fuel ethanol industry is also predicted to grow sharply in future, due to an increased interest in ethanol in Europe, Japan, the USA and several developing nations.

Butanediols including 1,2-butanediol, 1,3-butanediol, 1,4-butanediol and 2,3-butanediol may be considered to have a variety of advantages over ethanol. Like ethanol, butanediols may be used directly as an automotive fuel additive. They may also be relatively easily transformed into a number of other potentially higher value and/or higher energy products. For example, 2,3-butanediol may be readily converted in a two step process into an eight-carbon dimer which can be used as aviation fuel.

2,3-Butanediol derives its versatility from its di-functional backbone, i.e., 2 hydroxyl groups are located at vicinal C-atoms allowing the molecule to be transformed quite easily into substances such as butadiene, butadione, acetoin, methylethyl ketone etc. These chemical compounds are used as base molecules to manufacture a vast range of industrially produced chemicals.

In addition, 2,3-butanediol may be used as a fuel in an internal combustion engine. It is in several ways more similar to gasoline than it is to ethanol. As the interest in the production and application of environmentally sustainable fuels has strengthened, interest in biological processes to produce 2,3-butanediol (often referred to as bio-butanol) has increased.

2,3-Butanediol can be produced by microbial fermentation of carbohydrate containing feedstock (Syu M J, *Appl Microbiol Biotechnol* 55:10-18 (2001), Qin et al., *Chinese J Chem Eng* 14(1):132-136 (2006)). 2,3-Butanediol may also be produced by microbial fermentation of biomass from crops such as sugar beet, corn, wheat and sugarcane. However, the cost of these carbohydrate feed stocks is influenced by their value as human food or animal feed and the cultivation of starch or sucrose-producing crops for 2,3-butanediol production is not economically sustainable in all geographies. Therefore, it is of interest to develop technologies to convert lower cost and/or more abundant carbon resources into 2,3-butanediol.

Carbon Monoxide (CO) is a major by-product of the incomplete combustion of organic materials such as coal or oil and oil derived products. Although the complete combustion of carbon containing precursors yields $CO_2$ and water as the only end products, some industrial processes need elevated temperatures favouring the build up of carbon monoxide over $CO_2$. One example is the steel industry, where high temperatures are needed to generate desired steel qualities. For example, the steel industry in Australia is reported to produce and release into the atmosphere over 500,000 tonnes of CO annually.

Furthermore, CO is also a major component of syngas, where varying amounts of CO and $H_2$ are generated by gasification of a carbon-containing fuel. For example, syngas may be produced by cracking the organic biomass of waste woods and timber to generate precursors for the production of fuels and more complex chemicals.

The release of CO into the atmosphere may have significant environmental impact. In addition, emissions taxes may be required to be paid, increasing costs to industrial plants. Since CO is a reactive energy rich molecule, it can be used as a precursor compound for the production of a variety of chemicals. However, this valuable feedstock has not been utilised to produce 2,3-butanediol.

It is an object of the present invention to provide a process that goes at least some way towards overcoming the above disadvantages or at least to provide the public with a useful choice.

SUMMARY OF THE INVENTION

In one aspect, the invention provides a method of producing butanediol by microbial fermentation of a substrate comprising carbon monoxide. In particular embodiments, the invention provides a method of producing butanediol by microbial fermentation, the method comprising:
  a. providing a substrate comprising CO;
  b. in a bioreactor containing a culture of one or more micro-organisms, anaerobically fermenting the substrate to produce butanediol.

In certain embodiments, the butanediol is 2,3-butanediol.

In another aspect, the invention provides a method of increasing efficiency of 2,3-butanediol production by fermentation, the method including:
  a. providing a substrate comprising CO;
  b. in a bioreactor containing a culture of one or more micro-organisms, anaerobically fermenting the substrate to produce 2,3-butanediol.

In another aspect of the invention, there is provided a method of producing 2,3-butanediol by microbial fermentation, the method including:
  a. providing a substrate
  b. in a bioreactor containing a culture of one or more micro-organisms, anaerobically fermenting the substrate, wherein one or more micro-organisms includes one or more 2,3-butanediol dehydrogenase genes;

c. upregulating the 2,3-butanediol dehydrogenase gene(s), such that 2,3-butanediol is produced by the micro-organism(s).

In a further embodiment, the 2,3-butanediol is converted to a compound selected from the group consisting of butene(s), butadiene, methyl ethyl ketone (MEK) and mixtures thereof.

In another embodiment, the butene(s), butadiene or methyl ethyl ketone are further converted to a chemical product as will be detailed hereinafter.

In particular embodiments, the substrate comprises CO.

In particular embodiments of the various aspects, the substrate comprising carbon monoxide is a gaseous substrate comprising carbon monoxide. The gaseous substrate comprising carbon monoxide can be obtained as a by-product of an industrial process. In certain embodiments, the industrial process is selected from the group consisting of ferrous metal products manufacturing, non-ferrous products manufacturing, petroleum refining processes, gasification of biomass, gasification of coal, electric power production, carbon black production, ammonia production, methanol production and coke manufacturing. In one embodiment the gaseous substrate comprises a gas obtained from a steel mill. In another embodiment the gaseous substrate comprises automobile exhaust fumes.

In particular embodiments, the CO-containing substrate typically contains a major proportion of CO, such as at least about 20% to about 100% CO by volume, from 40% to 95% CO by volume, from 40% to 60% CO by volume, and from 45% to 55% CO by volume. In particular embodiments, the substrate comprises about 25%, or about 30%, or about 35%, or about 40%, or about 45%, or about 50% CO, or about 55% CO, or about 60% CO by volume. Substrates having lower concentrations of CO, such as 6%, may also be appropriate, particularly when $H_2$ and $CO_2$ are also present.

In particular embodiments of the various aspects, the substrate comprising CO is provided at a sufficient level, such that 2,3-butanediol is produced. In particular embodiments, CO is provided such that a specific uptake rate of at least 0.4 mmol/g/min; or at least 0.5 mmol/g/min; or at least 0.6 mmol/g/min; or at least 0.7 mmol/g/min; or at least 0.8 mmol/g/min; or at least 0.9 mmol/g/min; or at least 1.0 mmol/g/min; or at least 1.2 mmol/g/min; or at least 1.5 mmol/g/min is maintained or from about 0.4 mmol/g/min to about 1.5 mmol/g/min or from about 0.7 mmol/g/min to about 1.2 mmol/g/min.

In certain embodiments the one or more micro-organism is an acetogenic bacterium selected from *Clostridium autoethanogenum*, *Clostridium ljungdahlii*, *Clostridium thermoaceticum*, *Clostridium carboxidivorans*, and mixtures thereof.

In certain embodiments of the various aspects, the method comprises microbial fermentation using *Clostridium autoethanogenum*.

In another aspect, the invention provides a method of producing 2,3-butanediol by microbial fermentation, the method including:
a. providing a substrate
b. in a bioreactor including a culture of *Clostridium autoethanogenum*, anaerobically fermenting the substrate to produce 2,3-butanediol.

In particular embodiments, the substrate is one or more carbohydrates such as fructose. Alternatively the substrate comprises carbon monoxide. In another embodiment, the substrate is a gaseous substrate comprising carbon monoxide, as herein before described In a further aspect, the invention provides a method for producing butanediol by microbial fermentation of a first substrate and a second substrate comprising CO. Preferably, the butanediol is 2,3-butanediol.

In particular embodiments, the first substrate is a carbohydrate. In certain embodiments, the first substrate is fructose. In certain embodiments, the second substrate is a gaseous substrate comprising carbon monoxide, as herein before described.

In particular embodiments, the method includes the steps of:
(a) microbial fermentation of the first substrate to produce 2,3-butanediol
(b) microbial fermentation of the second substrate comprising CO to produce 2,3-butanediol.

In certain embodiments, steps (a) and (b) may be conducted at the same time. Alternatively, step (a) may substantially precede or follow step (b). In particular embodiments, the method may alternate between step (a) and step (b).

In a further aspect of the invention, there is provided a method according to any of the previous aspects, wherein the fermentation is carried out in a bioreactor.

In a further aspect of the invention, there is provided a method according to any of the previous aspects, wherein the method further includes the step of capturing or recovering the butanediol.

In a further aspect, there is provided butanediol, preferably 2,3-butanediol, produced by the methods of any of the previous aspects.

The invention may also be said broadly to consist in the parts, elements and features referred to or indicated in the specification of the application, individually or collectively, in any or all combinations of two or more of said parts, elements or features, and where specific integers are mentioned herein which have known equivalents in the art to which the invention relates, such known equivalents are deemed to be incorporated herein as if individually set forth.

DETAILED DESCRIPTION OF THE INVENTION

The following is a description of the present invention, including preferred embodiments thereof, given in general terms. The invention is further exemplified in the disclosure given under the heading "Examples" herein below, which provides experimental data supporting the invention, specific examples of aspects of the invention, and means of performing the invention.

As used herein "butanediol" refers to all structural isomers of the diol including 1,2-butanediol, 1,3-butanediol, 1,4-butanediol and 2,3-butanediol and stereoisomers thereof. The term "2,3-butanediol" should be interpreted to include all enantiomeric and diastereomeric forms of the compound, including (R,R), (S,S) and meso forms, in racemic, partially stereoisomerically pure and/or substantially stereoisomerically pure forms.

"Butene" (also known as butylene) as used herein, is intended to refer to all structural isomers of the alkene including 2-butene, but-1-ene, 2-methylpropene, and all stereoisomeric and geometric isomeric forms of the compound, including Z-but-2-ene, E-but-2-ene, in mixtures of isomers and pure and/or substantially pure forms.

As used herein, "butadiene" is intended to refer to all to all geometric isomers of the diene including cis and trans 1,3-butadiene, in mixtures of isomers and pure and/or substantially pure forms.

As used herein, "methyl ethyl ketone" (or MEK or butanone) is intended to refer to all isomers of the ketone in partially pure and/or substantially pure forms.

The term "bioreactor" includes a fermentation device consisting of one or more vessels and/or towers or piping arrangement, which includes the Continuous Stirred Tank Reactor (CSTR), Immobilized Cell Reactor (ICR), Trickle Bed Reactor (TBR), Bubble Column, Gas Lift Fermenter, Static Mixer, or other vessel or other device suitable for gas-liquid contact. As is described herein after, in some embodiments the bioreactor may comprise a first growth reactor and a second fermentation reactor. As such, when referring to the addition of a substrate, for example a substrate comprising carbon monoxide, to the bioreactor or fermentation reaction it should be understood to include addition to either or both of these reactors where appropriate.

The term "substrate comprising carbon monoxide" and like terms should be understood to include any substrate in which carbon monoxide is available to one or more strains of bacteria for growth and/or fermentation, for example.

"Gaseous substrates comprising carbon monoxide" include any gas which contains a level of carbon monoxide. The gaseous substrate will typically contain a major proportion of CO, preferably at least about 15% to about 95% CO by volume.

Unless the context requires otherwise, the phrases "fermenting", "fermentation process" or "fermentation reaction" and the like, as used herein, are intended to encompass both the growth phase and product biosynthesis phase of the process.

The inventors have surprisingly shown that 2,3-butanediol can be produced by microbial fermentation using *Clostridium autoethanogenum*. They have found that fermentation products include a variety of alcohols, whereby ethanol and 2,3-butanediol are significant substituents. 2,3-Butanediol has not been previously identified as a fermentation product using *Clostridium autoethanogenum*. In particular, the inventors have determined that *Clostridium autoethanogenum* can be used to produce 2,3-butanediol and other products from a substrate comprising carbohydrate. In particular, fructose can be converted into products including acetate, ethanol and 2,3-butanediol. It has also been surprisingly demonstrated that 2,3-butanediol can be produced by *Clostridium autoethanogenum* from substrates comprising CO, particularly gaseous substrates comprising CO. The use of a gaseous carbon source, particularly a source including CO, in fermentation processes has not previously resulted in the production of 2,3-butanediol.

In particular embodiments of the invention, the efficiency of 2,3-butaendiol production can be increased by providing the substrate at a sufficient level such that 2,3-butanediol is produced. It has been recognised that increasing the amount of substrate provided to a microbial culture, increases the amount of 2,3-butanediol produced by the culture.

In particular embodiments of the invention, the substrate comprising CO is provided at a sufficient level such that 2,3-butanediol is produced. It has been shown that a microbial culture comprising *C. autoethanogenum* can uptake CO at a rate up to approximately 1.5 to 2 mmol/gram dry weight microbial cells/minute (specific CO uptake). In particular embodiments of the invention, a substrate comprising CO is provided to the microbial culture comprising *C. autoethanogenum* such that a specific uptake is maintained substantially at or at least 0.4 mmol/g/min; or at least 0.5 mmol/g/min; or at least 0.6 mmol/g/min; or at least 0.7 mmol/g/min; or at least 0.8 mmol/g/min; or at least 0.9 mmol/g/min; or at least 1.0 mmol/g/min; or at least 1.2 mmol/g/min; or at least 1.5 mmol/g/min or from about 0.4 mmol/g/min to about 1.5 mmol/g/min or from about 0.7 mmol/g/min to about 1.2 mmol/g/min. In such embodiments, 2,3-butanediol is a significant fermentation product of at least 0.5 g/L; or at least 1 g/L; or at least 2 g/L; or at least 5 g/L. In particular embodiments, 2,3-butanediol is produced at a rate of at least 0.5 g/L/day; or at least 1 g/L/day.

In particular embodiments of the invention, apparatus used for conducting methods of the invention enable measurement and/or control of parameters such as CO supply, CO uptake, biomass level, 2,3-butanediol production. For example, samples can be taken from a bioreactor to determine one or more of the above parameters and the bioreactor conditions optionally adjusted to improve 2,3-butanediol production. For example, in a bioreactor, wherein the microbial culture is producing no or insignificant amounts of 2,3-butanediol, the CO supply can be increased such that CO uptake is increased and 2,3-butanediol is produced.

It is accepted that products such as acetate and ethanol are produced from CO via a combination of the acetyl-CoA cycle and the THF cycle as described in Phillips, J. R, et al, 1994, *Applied Biochemistry and Biotechnology*, 45/46: 145. However, in accordance with the methods of the invention, it has been surprisingly shown that 2,3-butanediol can be produced, particularly where CO is provided such that specific CO uptake rates of at least 0.4 mmol/g/min; or at least 0.5 mmol/g/min; or at least 0.6 mmol/g/min; or at least 0.7 mmol/g/min; or at least 0.8 mmol/g/min; or at least 0.9 mmol/g/min; or at least 1.0 mmol/g/min; or at least 1.2 mmol/g/min; or at least 1.5 mmol/g/min are maintained. Without wishing to be bound by theory, it is considered that by providing sufficient or elevated levels of CO, higher energy products, such as 2,3-butanediol can be produced during fermentation. It is considered precursors of products, such as 2,3-butanediol act as electron acceptors to relieve the microbial cell of excess reducing power, in the form of NAD(P)H, thus restoring a favourable NAD(P):NAD(P)H equilibrium. It is further considered that carbohydrates fermented by the culture can also be converted into 2,3-butanediol in a similar manner.

The following genes have been putatively identified in *C. autoethanogenum*: α-acetolactate synthase (ALS), α-acetolactate decarboxylase (ALDC) and 2,3-butanediol dehydrogenase (2,3BDH). The putative 2,3-butanediol dehydrogenase gene (ORF 1283) of *C. autoethanogenum* (strain deposited at DSMZ under the accession number 19630) shows strong homology to the 2,3BDH of *Clostridium novyi* (NT01CX_0344) with amino acid identities of 73% (262/357) and positives of 84% (300/357). ORF 1283 also shows significant homology to the gene YdjL (bdhA) of *Bacillus subtilis* (47% amino acid identities, 63% positives and E-value of 3e-89. Further evidence that ORF 1283 of LZ1560 is 2,3BDH comes from homology to 2,3BDH (YAL060W) of *Saccharomyces cerevisiae* (E=2e-53).

Without wishing to be bound by theory, it is considered 2,3-butanediol is produced from pyruvate (an intermediate in anabolism produced from acetyl CoA) as follows:

Real-Time PCR studies of 2,3-butanediol dehydrogenase in *C. autoethanogenum*, indicate that it is substantially upregulated in cultures where significant amounts of 2,3- butanediol are produced. Thus, 2,3-butanediol dehydrogenase can be upregulated in accordance with the methods of the invention. For example, where CO is supplied at sufficient levels, 2,3-butanediol dehydrogenase is upregulated. In particular, where CO is supplied such that the specific CO uptake by the microbial culture is at least 0.4 mmol/g/min; or at least 0.5 mmol/g/min; or at least 0.6 mmol/g/min; or at least 0.7 mmol/g/min; or at least 0.8 mmol/g/min; or at least 0.9 mmol/g/min; or at least 1.0 mmol/g/min; or at least 1.2 mmol/g/min; or at least 1.5 mmol/g/min; 2,3-butanediol dehydrogenase is upregulated. As such, the invention provides a method of producing 2,3-butanediol by microbial fermentation of a substrate by upregulation of 2,3-butanediol dehydrogenase.

The inventors have further demonstrated that different substrates, such as a carbohydrate substrate and a gaseous substrate comprising CO, can be switched during microbial production of 2,3-butanediol, without deleterious effect. In addition, they contemplate that substrates could be alternated, for example when one substrate is unavailable, and would continue to produce 2,3-butanediol.

In accordance with the results obtained, in one embodiment of the invention, 2,3-butanediol is produced by microbial fermentation of a substrate comprising carbohydrate. In another embodiment of the invention, a substrate comprising carbon monoxide, preferably a gaseous substrate comprising CO, is converted into various products including 2,3-butanediol, by *Clostridium autoethanogenum*.

In a further embodiment of the invention, a first substrate comprising carbohydrate (preferably fructose) may be used in initial stages of the fermentation reaction and following complete consumption of the substrate, the substrate can be switched to a second substrate comprising CO. Again, the inventors have surprisingly determined that 2,3-butanediol is produced in the initial stages where the first substrate comprising carbohydrate is the sole carbon source and is also produced in the latter stages where the substrate comprising CO is the sole carbon source.

The inventors have shown that 2,3-butanediol is produced under a variety of conditions, including media containing alternative buffer solutions such as acetate buffer and citrate buffer. The inventors also submit that in embodiments where the pH is uncontrolled and may be variable, 2,3-butanediol is still produced. Examples of media suitable for carrying out the desired fermentation are described in the examples section hereinafter.

The inventors contemplate that the 2,3-butanediol produced in such processes may be readily recovered using separation techniques known in the art. Furthermore, the 2,3-butanediol may be readily converted into substances such as butadiene, butadione, acetoin, methylethyl ketone and the like. Such chemical compounds are valuable base molecules used to manufacture a significant percentage of all chemical industry products. Therefore, the inventors contemplate that the 2,3-butanediol produced in the processes disclosed herein may be used in the manufacture of a wide range of well known industrial products.

The invention is generally described herein in relation to preferred embodiments of the invention which utilise *Clostridium autoethanogenum* and/or produce 2,3-butanediol. However, it should be appreciated that alternative micro-organisms may be substituted for *C. autoethanogenum*. Similarly, the methods may be used to produce and recover butanediols other than 2,3-butanediol. Accordingly, unless the context requires otherwise, reference to "2,3-butanediol" may be substituted by the general term "butanediol".

Method

In one embodiment, the invention provides a method for the production of butanediol by microbial fermentation. In a preferred embodiment the method comprises at least the step of anaerobically fermenting a substrate comprising CO, preferably a gaseous substrate comprising CO, to obtain 2,3-butanediol.

In a particular embodiment of the invention, the method includes the steps of:
 (a) providing a substrate comprising CO, preferably a gaseous substrate comprising CO;
 (b) in a bioreactor containing a culture of one or more micro-organisms anaerobically fermenting the substrate to produce 2,3-butanediol.

In another embodiment, the invention provides a method of increasing efficiency of 2,3-butanediol production by fermentation, the method including:
 (a) providing a substrate comprising CO;
 (b) in a bioreactor containing a culture of one or more micro-organisms, anaerobically fermenting the substrate to produce 2,3-butanediol.

In particular embodiments, the substrate comprising CO is provided at a level sufficient to produce significant amounts of 2,3-butanediol, such as at least 0.5 g/L of fermentation media, or at least 1 g/L, or at least 2 g/L, or at least 5 g/L. In certain embodiments, CO is provided at a level sufficient to produce 2,3-butanediol at a rate of at least 0.5 g/L/day; or at least 1 g/L/day. In particular embodiments, CO is provided such that a specific uptake rate of at least 0.4 mmol/g/min; or at least 0.5 mmol/g/min; or at least 0.6 mmol/g/min; or at least 0.7 mmol/g/min; or at least 0.8 mmol/g/min; or at least 0.9 mmol/g/min; or at least 1.0 mmol/g/min; or at least 1.2 mmol/g/min; or at least 1.5 mmol/g/min is maintained. Those skilled in the art will appreciate methods of supplying CO, particularly gaseous CO, such that the required uptake rate is achieved. However, by way of example, factors such as increasing gas hold-up in a fermentation media will increase the amount of CO available for conversion to products by the microbial culture. Gas hold-up can typically be increased by mechanical means, such as increasing agitation in a CSTR. Furthermore, supplying CO at a faster rate or a higher partial pressure will also increase the CO availability in a fermentation broth.

In another embodiment, the method involves fermentation of a substrate comprising carbohydrate by *Clostridium autoethanogenum* to produce butanediol, preferably, 2,3-butanediol.

In another embodiment, the method includes the steps of:
 (a) microbial fermentation of the first substrate to produce 2,3-butanediol
 (b) microbial fermentation of the second substrate comprising CO to produce 2,3-butanediol.

In certain embodiments, the first substrate is carbohydrate and in some embodiments, the substrate is fructose. Preferably, the second substrate is a gaseous substrate comprising CO. In particular embodiments, steps (a) and (b) may be conducted at the same time. Alternatively, step (a) may substantially precede or follow step (b). Preferably, the method may alternate between step (a) and step (b).

In certain embodiments of the invention, the method further includes the step of capturing or recovering the 2,3-butanediol produced.

Micro-Organisms

In embodiments of the invention the one or more micro-organisms used in the fermentation is an acetogenic bacterium selected from the group consisting of *Clostridium autoethanogenum Clostridium ljungdahlii, Clostridium thermoaceticum, Clostridium carboxidivorans*, and mixtures thereof. In a preferred embodiment the acetogenic bacterium is *Clostridium autoethanogenum*. In a more preferred embodiment the *Clostridium autoethanogenum* is a *Clostridium autoethanogenum* having the identifying characteristics of the strain deposited at the German Resource Centre for Biological Material (DSMZ) under the identifying deposit number 19630. In another embodiment the *Clostridium autoethanogenum* is a *Clostridium autoethanogenum* having the identifying characteristics of DSMZ deposit number DSMZ 10061.

Culturing of the bacteria used in a method of the invention may be conducted using any number of processes known in the art for culturing and fermenting substrates using anaerobic bacteria. Exemplary techniques are provided in the "Examples" section of this document. By way of further example, those processes generally described in the following articles using gaseous substrates for fermentation may be utilised: K. T. Klasson, M. D. Ackerson, E. C. Clausen and J. L. Gaddy (1991). Bioreactors for synthesis gas fermentations resources. Conservation and Recycling, 5; 145-165; K. T. Klasson, M. D. Ackerson, E. C. Clausen and J. L. Gaddy (1991). Bioreactor design for synthesis gas fermentations. Fuel. 70. 605-614; K. T. Klasson, M. D. Ackerson, E. C. Clausen and J. L. Gaddy (1992). Bioconversion of synthesis gas into liquid or gaseous fuels. Enzyme and Microbial Technology. 14; 602-608; J. L. Vega, G. M. Antorrena, E. C. Clausen and J. L. Gaddy (1989). Study of Gaseous Substrate Fermentation: Carbon Monoxide Conversion to Acetate. 2. Continuous Culture. Biotech. Bioeng. 34. 6. 785-793; J. L. Vega, E. C. Clausen and J. L. Gaddy (1989). Study of gaseous substrate fermentations: Carbon monoxide conversion to acetate. 1. Batch culture. Biotechnology and Bioengineering. 34. 6. 774-784; and, J. L. Vega, E. C. Clausen and J. L. Gaddy (1990). Design of Bioreactors for Coal Synthesis Gas Fermentations. Resources, Conservation and Recycling. 3. 149-160. Methods for culturing bacteria on substrates comprising carbohydrates are also well known in the art.

Substrates

In one embodiment of the invention, 2,3-butanediol is produced by microbial fermentation of a substrate comprising carbohydrate using *Clostridium autoethanogenum*. It will be appreciated there are many examples of carbohydrates suitable for fermentation known in the art and many examples of the types of processes used to ferment the carbohydrate substrate. By way of example, suitable substrates may include, but are not limited to, monosaccharides such as glucose and fructose, oligosaccharides such as sucrose or lactose, polysaccharides, such as cellulose or starch. Although it is contemplated that any of these carbohydrate substrates (and mixtures thereof) are suitable in the present invention, preferred carbohydrate substrates are fructose and sucrose (and mixtures thereof).

Those skilled in the art will appreciate fermentable sugars may be obtained from cellulosic and lignocellulosic biomass through processes of pre-treatment and saccharification, as described, for example, in US20070031918. Biomass refers to any cellulose or lignocellulosic material and includes materials comprising cellulose, and optionally further comprising hemicellulose, lignin, starch, oligosaccharides and/or monosaccharides. Biomass includes, but is not limited to bioenergy crops, agricultural residues, municipal solid waste, industrial solid waste, sludge from paper manufacture, yard waste, wood and forestry waste. However, in exemplary embodiments of the invention commercially available fructose is used as the carbon and energy source for the fermentation.

In a particular embodiment, a substrate comprising carbon monoxide, preferably a gaseous substrate comprising carbon monoxide is used in the methods of the invention. The gaseous substrate may be a waste gas obtained as a by-product of an industrial process, or from some other source such as from combustion engine (for example automobile) exhaust fumes. In certain embodiments, the industrial process is selected from the group consisting of ferrous metal products manufacturing, such as a steel mill, non-ferrous products manufacturing, petroleum refining processes, gasification of coal, electric power production, carbon black production, ammonia production, methanol production and coke manufacturing. In these embodiments, the CO-containing gas may be captured from the industrial process before it is emitted into the atmosphere, using any convenient method. Depending on the composition of the gaseous substrate comprising carbon monoxide, it may also be desirable to treat it to remove any undesired impurities, such as dust particles before introducing it to the fermentation. For example, the gaseous substrate may be filtered or scrubbed using known methods.

In other embodiments of the invention, the gaseous substrate comprising carbon monoxide may be sourced from the gasification of biomass. The process of gasification involves partial combustion of biomass in a restricted supply of air or oxygen. The resultant gas typically comprises mainly CO and $H_2$, with minimal volumes of $CO_2$, methane, ethylene and ethane. For example, biomass by-products obtained during the extraction and processing of foodstuffs such as sugar from sugarcane, or starch from maize or grains, or non-food biomass waste generated by the forestry industry may be gasified to produce a CO-containing gas suitable for use in the present invention.

The CO-containing substrate will typically contain a major proportion of CO, such as at least about 20% to about 100% CO by volume, from 40% to 95% CO by volume, from 40% to 60% CO by volume, and from 45% to 55% CO by volume. In particular embodiments, the substrate comprises about 25%, or about 30%, or about 35%, or about 40%, or about 45%, or about 50% CO, or about 55% CO, or about 60% CO by volume. Substrates having lower concentrations of CO, such as 6%, may also be appropriate, particularly when $H_2$ and $CO_2$ are also present.

In particular embodiments, CO is supplied at a level sufficient for 2,3-butanediol production to occur. In particular embodiments, CO is provided such that a specific uptake rate of at least 0.4 mmol/g/min; or at least 0.5 mmol/g/min; or at least 0.6 mmol/g/min; or at least 0.7 mmol/g/min; or at least 0.8 mmol/g/min; or at least 0.9 mmol/g/min; or at least 1.0 mmol/g/min; or at least 1.2 mmol/g/min; or at least 1.5 mmol/g/min is maintained. Those skilled in the art will appreciate methods of supplying CO, particularly gaseous CO, such that the required uptake rate is achieved. However, by way of example, factors such as increasing gas hold-up in a fermentation media will increase the amount of CO available for conversion to products by the microbial culture. Those skilled in the art will appreciate methods of increasing gas hold-up. However, by way of non-limiting example, gas hold-up is typically increased by mechanical means such as increasing agitation in a CSTR. Furthermore, supplying CO at a faster rate or a higher partial pressure will also increase the CO availability in a fermentation broth.

It is not necessary for the gaseous substrate to contain any hydrogen, however this is not considered detrimental to 2,3-butanediol production. The gaseous substrate may also contain some $CO_2$ for example, such as about 1% to about 80% by volume, or 1% to about 30% by volume. In one embodiment it contains about 5% to about 10% by volume. In another embodiment the gaseous substrate contains approximately 20% $CO_2$ by volume.

Typically, the carbon monoxide will be added to the fermentation reaction in a gaseous state. However, the invention should not be considered to be limited to addition of the substrate in this state. For example, the carbon monoxide could be provided in a liquid. For example, a liquid may be saturated with a carbon monoxide containing gas and then that liquid added to a bioreactor. This may be achieved using standard methodology. By way of example a microbubble dispersion generator (Hensirisak et. al. Scale-up of microbubble dispersion generator for aerobic fermentation; *Applied Biochemistry and Biotechnology* Volume 101, Number 3/October, 2002) could be used.

In one embodiment of the invention, the inventors have determined that 2,3-butanediol can be produced by fermentation of a first substrate and a second substrate. In one particular embodiment of the invention, 2,3-butanediol will be produced when a first substrate, for example a carbohydrate such as fructose and a second substrate, preferably a substrate comprising CO, are provided.

In a further embodiment, the inventors have determined that 2,3-butanediol will be produced by a first substrate and on complete consumption, the first substrate may be replaced with a second substrate and the 2,3-butanediol continues to be produced. In a particular embodiment, the first substrate is fructose and on complete consumption of the fructose, a substrate comprising CO can be provided. The inventors have surprisingly found that 2,3-butanediol continues to be produced. The inventors further contemplate that the first substrate and second substrate may be alternated if needed. For example if a first substrate is unavailable, an alternative substrate may be used until the availability of the first substrate improves.

Media

It will be appreciated that for growth of the bacteria and substrate to butanediol fermentation to occur, in addition to the substrate, a suitable nutrient medium will need to be fed to the bioreactor. A nutrient medium will contain components, such as vitamins and minerals, sufficient to permit growth of the micro-organism used. Anaerobic media suitable for the growth of *Clostridium autoethanogenum* are known in the art, as described for example by Abrini et al (*Clostridium autoethanogenum*, sp. November, An Anaerobic Bacterium That Produces Ethanol From Carbon Monoxide; *Arch. Microbiol.*, 161: 345-351 (1994)). The "Examples" section herein after provides further examples of suitable media.

Fermentation Conditions

The fermentation should desirably be carried out under appropriate conditions for the substrate to butanediol fermentation to occur. Reaction conditions that should be considered include temperature, media flow rate, pH, media redox potential, agitation rate (if using a continuous stirred tank reactor), inoculum level, maximum substrate concentrations and rates of introduction of the substrate to the bioreactor to ensure that substrate level does not become limiting, and maximum product concentrations to avoid product inhibition. Examples of fermentation conditions suitable for anaerobic fermentation of a substrate comprising CO are detailed in WO2007/117157, WO2008/115080, WO2009/022925 and WO2009/064200, the disclosure of which are incorporated herein by reference. It is recognised the fermentation conditions reported therein can be readily modified in accordance with the methods of the instant invention.

The optimum reaction conditions will depend partly on the particular microorganism of used. However, in general, it is preferred that the fermentation be performed at a pressure higher than ambient pressure. Operating at increased pressures allows a significant increase in the rate of CO transfer from the gas phase to the liquid phase where it can be taken up by the micro-organism as a carbon source for the production of 2,3 butanediol. This in turn means that the retention time (defined as the liquid volume in the bioreactor divided by the input gas flow rate) can be reduced when bioreactors are maintained at elevated pressure rather than atmospheric pressure.

Also, since a given CO-to-product conversion rate is in part a function of the substrate retention time, and achieving a desired retention time in turn dictates the required volume of a bioreactor, the use of pressurized systems can greatly reduce the volume of the bioreactor required, and consequently the capital cost of the fermentation equipment. According to examples given in U.S. Pat. No. 5,593,886, reactor volume can be reduced in linear proportion to increases in reactor operating pressure, i.e. bioreactors operated at 10 atmospheres of pressure need only be one tenth the volume of those operated at 1 atmosphere of pressure.

The benefits of conducting a gas-to-product fermentation at elevated pressures have also been described elsewhere. For example, WO 02/08438 describes gas-to-ethanol fermentations performed under pressures of 30 psig and 75 psig, giving ethanol productivities of 150 g/l/day and 369 g/l/day respectively. However, example fermentations performed using similar media and input gas compositions at atmospheric pressure were found to produce between 10 and 20 times less ethanol per liter per day.

It is also desirable that the rate of introduction of the CO-containing gaseous substrate is such as to ensure that the concentration of CO in the liquid phase does not become limiting. This is because a consequence of CO-limited conditions may be that the 2,3 butanediol product is consumed by the culture.

The inventors have determined that, in one embodiment where pH is not controlled, there does not appear to be a deleterious effect on 2,3-butanediol production.

Bioreactor

Fermentation reactions may be carried out in any suitable bioreactor as described previously herein. In some embodiments of the invention, the bioreactor may comprise a first, growth reactor in which the micro-organisms are cultured, and a second, fermentation reactor, to which broth from the growth reactor is fed and in which most of the fermentation product (2,3-butanediol, for example) is produced.

Product Recovery

The fermentation will result in a fermentation broth comprising a desirable product (such as butanediol) and/or one or more by-products (such as ethanol, acetate and butyrate) as well as bacterial cells, in a nutrient medium. In a preferred embodiment, the fermentation products include 2,3-butanediol.

2,3-butanediol, or a mixed alcohol stream containing 2,3-butanediol and one or more other alcohols, may be recovered from the fermentation broth by methods known in the art, such as fractional distillation or evaporation, pervaporation, and extractive fermentation. By-products such as acids including acetate and butyrate may also be recovered from the fermentation broth using methods known in the art. For example, an adsorption system involving an activated charcoal filter or electrodialysis may be used.

In certain embodiments of the invention, 2,3-butanediol and by-products are recovered from the fermentation broth by continuously removing a portion of the broth from the bioreactor, separating microbial cells from the broth (conveniently by filtration, for example), and recovering 2,3-butanediol and optionally other alcohols and acids from the broth. Alcohols may conveniently be recovered for example by distillation, and acids may be recovered for example by adsorption on activated charcoal. The separated microbial cells are preferably returned to the fermentation bioreactor. The cell free permeate remaining after the alcohol(s) and acid(s) have been removed is also preferably returned to the fermentation bioreactor. Additional nutrients (such as B vitamins) may be added to the cell free permeate to replenish the nutrient medium before it is returned to the bioreactor.

Also, if the pH of the broth was adjusted during recovery of 2,3-butanediol and/or by-products, the pH should be re-adjusted to a similar pH to that of the broth in the fermentation bioreactor, before being returned to the bioreactor.

Conversion to Chemical Products

A number of known methods may be used for the production of MEK from 2,3 butanediol. For example, MEK can be obtained by the direct dehydration of 2,3-butanediol over a variety of catalysts (sulphuric acid, Cu, AlO3, Zeolite etc): for an example see Emerson et. al. (1982).

A number of known methods may be used for the production of butene(s) from 2,3 butanediol. For example, treatment of the diol with HBr, followed by Zn powder results in but-2-ene. The debrominations proceed with a high degree of anti stereospecificity (House and Ro, 1958; Gordon and Hay, 1968), the meso isomer giving the trans butene, and the (+) isomer the cis butene.

A number of known methods may be used for the production of butadiene from 2,3 butanediol. For example, butenes can be catalytically dehydrogenated to 1,3-butadiene in the presence of superheated steam as a diluent and a heating medium (Kearby, 1955). By way of further example, butadiene can also be obtained by the direct dehydration of 2,3-butanediol over thoria catalyst, although most other dehydration catalysts give methyl ethyl ketone as the main product (Winfield, 1945).

Butadiene, butene(s), and MEK can subsequently be used in a variety of processes for producing commercially useful products.

For example, butene(s) may be used in the production of gasoline and butadiene. By way of yet further example, butene(s) may be used as a component or precursor in the manufacture of C12 paraffins, such as iso paraffins used as aviation fuels (see U.S. Pat. No. 7,338,541, for example).

MEK dissolves many substances and may be used, for example, as a solvent in processes involving gums, resins, cellulose acetate, and nitrocellulose coatings and in vinyl films. For this reason it finds use, for example, in the manufacture of plastics, textiles, paraffin wax, and in household products such as lacquer, varnishes and paint remover, glues, and as a cleaning agent. It also has use as a denaturing agent for denatured alcohol. By way of further example, it may also be used in dry erase markers as the solvent of the erasable dye. In addition, MEK is the precursor to methyl ethyl ketone peroxide, a catalyst used in some polymerization reactions. Further, MEK can be converted to 2-butanol by contacting the MEK with a catalyst such as ruthenium on carbon.

Butadiene may be used, for example, to produce synthetic rubbers and polymer resins. While polybutadiene itself is a very soft, almost liquid material, polymers prepared from mixtures of butadiene with styrene or acrylonitrile, such as ABS, are both tough and elastic. Styrene-butadiene rubber is the material most commonly used for the production of automobile tires. Butadiene may also be used to make nylon via the intermediate adiponitrile, other synthetic rubber materials such as chloroprene, and the solvent sulfolane. In addition, butadiene may be used in the industrial production of 4-vinylcyclohexene via a dimerization reaction and cyclododecatriene via a trimerization reaction. Butadiene is also useful in the synthesis of cycloalkanes and cycloalkenes, as it reacts with double and triple carbon-carbon bonds through the Diels-Alder reaction. By way of further example, butadiene may be used in the manufacture of cycloalkanes, cycloalkenes, dodecandioic acid (DDDA), Adiponitrile, Caprolactam, styrene, ethylidene norbornene, lauryl lactam and 1,5-cyclooctadiene (COD).

It should be appreciated that the methods of the invention may be integrated or linked with one or more methods for the production of downstream products from butene(s), butadiene and/or MEK. For example, the methods of the invention may feed butene(s), butadiene and/or MEK directly or indirectly to chemical processes or reactions sufficient for the conversion or production of other useful chemical products. In some embodiments, as noted herein before, 2,3 butanediol is converted to one or more chemical products directly via the intermediate compounds butene(s), butadiene and/or MEK without the need for recovery of butene(s), butadiene and/or MEK from the method before subsequent use in production of the one or more chemical products.

In particular embodiments, 2,3-butanediol is converted to butene(s), butadiene and/or MEK by one or more chemical processes, which in turn is converted to one or more chemical products by one or more chemical processes. In particular embodiments, the one or more chemical products are produced without recovering the butene(s), butadiene and/or MEK. In another embodiment, 2,3-butanediol is converted to one or more chemical products in a single chemical process via one or more of the butene(s), butadiene and/or MEK intermediate compounds.

The invention will now be described in more detail with reference to the following non-limiting examples.

EXAMPLES

Materials and Methods

| Solution A | |
|---|---|
| $NH_4Ac$ | 3.083 g |
| $MgCl_2 \cdot 6H_2O$ | 0.61 g |
| $CaCl_2 \cdot 2H_2O$ | 0.294 g |
| KCl | 0.15 g |
| NaCl (optional) | 0.12 g |
| Distilled Water | Up to 1 L |
| Solution B | |
| Biotin | 20.0 mg |
| Folic acid | 20.0 mg |
| Pyridoxine•HCl | 10.0 mg |
| Thiamine•HCl | 50.0 mg |
| Riboflavin | 50.0 mg |
| Nicotinic acid | 50.0 mg |
| Calcium D-(*)-pantothenate | 50.0 mg |
| Vitamin B12 | 50.0 mg |
| p-Aminobenzoic acid | 50.0 mg |
| Thioctic acid | 50.0 mg |
| Distilled water | To 1 Liter |
| Solution(s) C | |
| Component/0.1M solution (aq) | Quantity/ml into 1 L media |
| $FeCl_3$ | 1 ml |
| $CoCl_2$ | 0.5 ml |

-continued

|  | |
|---|---|
| NiCl$_2$ | 0.5 ml |
| H$_3$BO$_3$ | 0.1 ml |
| Na$_2$MoO$_4$ | 0.1 ml |
| MnCl$_2$ | 0.1 ml |
| Na$_2$WO$_4$ | 0.1 ml |
| ZnCl$_2$ | 0.1 ml |
| Na$_2$SeO$_3$ | 0.1 ml |

| Media Component | Solution D Concentration per 1.0 L of Media | Solution E Concentration per 1.0 L of Media |
|---|---|---|
| MgCl$_2$•6H$_2$O | 0.5 g | 0.5 g |
| NaCl | 0.2 g | 0.2 g |
| CaCl$_2$ | 0.2 g | 0.2 g |
| 100 mM sodium phosphate buffer (pH 6.0) | — | 160 mL |
| NaH$_2$PO$_4$ | 2.04 g | — |
| NH$_4$Cl | 2.5 g | 0.6 g |
| 85% H$_3$PO$_4$ | — | 0.5 mL |
| KCl | 0.15 g | 0.15 g |
| Solution C | 10 mL | 10 mL |
| Solution E | 10 mL | 10 mL |
| Resazurin (1000 mg/L stock) | 2 mL | 1 mL |
| FeCl$_3$ | 0.01 g | 0.0025 g |
| Cysteine HCl monohydrate | 0.5 g | 0.25 g |
| Agarose (optional) | 15 g | — |
| Distilled water | To 1 Liter | To 1 Liter |

| Solution F | |
|---|---|
| Composite trace metal solution | per L of stock |
| Nitrilotriacetic Acid | 1.5 g |
| MgSO$_4$•7H$_2$O | 3.0 g |
| MnSO$_4$•H$_2$O | 0.5 g |
| NaCl | 1.0 g |
| FeSO$_4$•7H$_2$O | 0.1 g |
| Fe(SO$_4$)$_2$(NH$_4$)$_2$•6H$_2$O | 0.8 g |
| CoCl$_2$•6H$_2$O | 0.2 g |
| ZnSO$_4$•7H$_2$O | 0.2 g |
| CuCl$_2$•2H$_2$O | 0.02 g |
| AlK(SO$_4$)$_2$•12H$_2$O | 0.02 g |
| H$_3$BO$_3$ | 0.30 g |
| NaMoO$_4$•2H$_2$O | 0.03 g |
| Na$_2$SeO$_3$ | 0.02 g |
| NiCl$_2$•6H$_2$O | 0.02 g |
| Na$_2$WO$_4$•6H$_2$O | 0.02 g |
| Distilled water | To 1 Liter |

Preparation of Na$_2$S$_x$

A 500 ml flask was charged with Na$_2$S (93.7 g, 0.39 mol) and 200 ml H$_2$O. The solution was stirred until the salt had dissolved and sulfur (25 g, 0.1 mol) was added under constant N$_2$ flow. After 2 hours stirring at room temperature, the "Na$_2$S$_x$" solution (approx 4M with respect to [Na] and approx 5M with respect to sulfur), now a clear reddish brown liquid, was transferred into N$_2$ purged serum bottles, wrapped in aluminium foil.

Preparation of Cr (II) Solution

A 1 L three necked flask was fitted with a gas tight inlet and outlet to allow working under inert gas and subsequent transfer of the desired product into a suitable storage flask. The flask was charged with CrCl$_3$.6H$_2$O (40 g, 0.15 mol), zinc granules [20 mesh] (18.3 g, 0.28 mol), mercury (13.55 g, 1 mL, 0.0676 mol) and 500 mL of distilled water. Following flushing with N$_2$ for one hour, the mixture was warmed to about 80° C. to initiate the reaction. Following two hours of stirring under a constant N$_2$ flow, the mixture was cooled to room temperature and continuously stirred for another 48 hours by which time the reaction mixture had turned to a deep blue solution. The solution was transferred into N$_2$ purged serum bottles and stored in the fridge for future use.

Bacteria:

The *Clostridium autoethanogenum* used is that deposited at the German Resource Centre for Biological Material (DSMZ) and allocated the accession number 19630.

Sampling and Analytical Procedures

Media samples were taken from the fermentation reactor (e.g. CSTR or serum bottle) at intervals over the course of the fermentation. Each time the media was sampled care was taken to ensure that no gas was allowed to enter into or escape from the reactor.

HPLC:

HPLC System Agilent 1100 Series. Mobile Phase: 0.0025N Sulfuric Acid. Flow and pressure: 0.800 mL/min. Column: Alltech IOA; Catalog #9648, 150×6.5 mm, particle size 5 μm. Temperature of column: 60° C. Detector: Refractive Index. Temperature of detector: 45° C.

Method for Sample Preparation:

400 μL of sample and 50 μL of 0.15M ZnSO$_4$ and 50 μL of 0.15M Ba(OH)$_2$ are loaded into an Eppendorf tube. The tubes are centrifuged for 10 min. at 12,000 rpm, 4° C. 200 μL of the supernatant are transferred into an HPLC vial, and 5 μL are injected into the HPLC instrument.

Headspace Analysis:

Measurements were carried out on a Varian CP-4900 micro GC with two installed channels. Channel 1 was a 10 m Molsieve column running at 70° C., 200 kPa argon and a backflush time of 4.2 s, while channel 2 was a 10 m PPQ column running at 90° C., 150 kPa helium and no backflush. The injector temperature for both channels was 70° C. Runtimes were set to 120 s, but all peaks of interest would usually elute before 100 s. Specific CO uptake was determined by calculating CO consumption per gram of cells (dry weight—see below).

Cell Density:

Cell density was determined by counting bacterial cells in a defined aliquot of fermentation broth. Alternatively, the absorbance of the samples was measured at 600 nm (spectrophotometer) and the dry weight determined via calculation according to published procedures.

Metal Sulfide Solution 1:

Approximately 950 mL of solution A was transferred into a 1 L fermenter and sparged with nitrogen. H$_3$PO$_4$ (85% solution, 1.5 mL) was added and the pH adjusted to 5.3 using concentrated NH$_4$OH(aq). Resazurin (1 mL of a 2 g/L solution) was added and the solution sparged with N2. Chromium (II)chloride was added until the ORP of the solution decreased to approximately −150 mV. 10× Solution(s) C were added before sodium polysulfide (1.44 mL of a 4.3M or 1 mL of a 6M solution) were added and the solution sparged with N2.

Example 1A

Production of 2,3-Butanediol by Fermentation

Fermentive conversion of a substrate, using *Clostridium autoethanogenum* was conducted in a CSTR reactor over a two week period, with periodic monitoring. The media used for the CSTR experiments were prepared in accordance with the components listed in Table E. The phosphate salt mixture consisted of 0.65 mM Na$_2$HPO4 and 15.3 mM NaH$_2$PO$_4$. All other components such as the phosphoric acid, the ammonium salts and the cysteine-hydrochloride were mixed into 800 ml of water before the buffer salts were added to the solution. Proceeding in this manner ensured that the pH increased above about 6.5 avoiding the precipitation of media components. The solution was diluted to 1 L and made anaerobic by heating to boiling and allowing it to cool to room temperature under a constant flow of N2 gas. Once cool, the solution was adjusted to the final pH of 5.3 and the B vitamins added. Anaerobicity was maintained throughout the experiment. Carbohydrate (5 g/L fructose) was added to the basic media formulation. The media solutions were introduced into the fermenters and optionally sparged with the respective CO containing gases from the start of the experiment, or after a predetermined interval. During these experiments, the pH was controlled to remain at 5.5 by adding an aqueous solution of NaOH. An actively growing *Clostridium autoethanogenum* culture was inoculated into the reactor at a level of 5% (v/v). The temperature of the reactor was maintained at 37° C. and agitation rate was 400 rpm.

Results:

Initially, the fermentation contained fructose as a substrate, which resulted in the production of acetic acid, ethanol and 2,3-butanediol. Over time, the fructose was consumed and a gas stream including CO (95% CO, 5% CO2) was sparged through the media. The media was maintained at pH 5.5 (Table 1). It should be noted that even when the carbohydrate had been consumed, the above mentioned products increased in concentration, clearly demonstrating that the CO was used to produce the products including 2,3-butanediol.

TABLE 1

Monitoring of production of 2,3-butanediol, ethanol and acetate (concentrations in g/L) over time in a CSTR reactor.

| Time\hours | Fructose | Acetic acid | Ethanol | 2,3-Butanediol |
|---|---|---|---|---|
| 0 | 5 | 0 | 0 | 0 |
| 23 | 5 | 0.123 | 0.018 | 0 |
| 45 | 3.8 | 0.579 | 0.167 | 0.05 |
| 110 | 0 | 4.753 | 2.8 | 1.2 |
| 185 | 0 | 7.2 | 3.8 | 1.9 |
| 324 | 0 | 6.736 | 4.9 | 1.91 |

Example 1B

Production of 2,3-Butanediol by Fermentation

In a further experiment, the conversion of a substrate by *Clostridium autoethanogenum* was conducted in a CSTR reactor over a 10 day period, with periodic monitoring. In this instance the fermenter and media were prepared in accordance with Example 1A, however the substrate was exclusively simulated steel mill gas (70% CO, 1% H2, 14% N2, 15% CO2) sparged continuously and the pH of the media was kept constant at 5.5 (Table 2). Conversion of the substrate again resulted in acetic acid, ethanol and 2,3-butanediol, demonstrating that even in the absence of a carbohydrate substrate at the commencement of the fermentation, acetic acid, ethanol and butanediol are produced.

TABLE 2

Monitoring of production of 2,3-butanediol, ethanol and acetate (concentrations in g/L) over time in a CSTR batch reactor.

| Time\days | Acetic acid | Ethanol | 2,3-Butanediol |
|---|---|---|---|
| 0 | 0 | 0 | 0 |
| 6 | 4.5 | 0.5 | 0 |
| 10 | 5 | 4 | 0.5 |

Example 2

Production of 2,3-Butanediol by Fermentation

In a further experiment, the conversion of a substrate by *Clostridium autoethanogenum* was conducted in a CSTR reactor over a 3 day period, with periodic monitoring. In this instance, the fermenter and media were prepared in accordance with that described in Example 1A, however the substrate was simulated steel mill gas (70% CO, 1% H2, 14% N2, 15% CO2), sparged continuously and fructose (10 g/L) and the pH of the media was kept constant at 5.5 (Table 3). Conversion of the substrate again resulted in acetic acid, ethanol and 2,3-butanediol.

TABLE 3

Monitoring of production of 2,3-butanediol, ethanol and acetate (concentrations in g/L) over time in a CSTR batch reactor.

| Time\hours | Fructose | Acetic acid | Ethanol | 2,3-Butanediol |
|---|---|---|---|---|
| 0 | 10 | 0 | 0 | 0 |
| 15 | 9.8 | 0.8 | 0.2 | 0.05 |
| 23 | 8.87 | 1.7 | 0.7 | 0.2 |
| 39 | 5.3 | 3.7 | 2.3 | 0.9 |
| 69 | 1.8 | 7.3 | 4 | 3.1 |

The final concentrations of acetate, ethanol and 2,3-butanediol were also compared between the fermenter experiments outlined in Examples 1A, 1B and 2, at the end of each experiment (note, these results relate to the final concentrations measured in tables 1-3 and are summarised for comparison in Table 4).

TABLE 4

Examples of 2,3-butanediol production using alternative substrates in a CSTR reactor, measured on conclusion of each experiment. Results are given in g/L.

| Substrate | Final Acetate | Final Ethanol | Final 2,3-Butanediol | Fermentation time (days) |
|---|---|---|---|---|
| Fructose then Mill gas (Ex 1A) | 6.7 | 4.9 | 1.9 | 13.5 |
| Mill gas only (Ex 1B) | 5 | 4 | 0.5 | 10 |
| Fructose and Mill gas (Ex 2) | 7.3 | 4 | 3.1 | 2.9 |

Example 3

Production of 2,3-Butanediol by Fermentation

In order to ascertain how media conditions may affect the production of 2,3-butanediol, serum bottles containing media comprising a selection of buffers were prepared and the fermentation products analysed at the end of the experiment (Table 5). Incubation was performed in 234 ml sealed serum bottles each containing 50 ml of the above described media (Table E), optionally buffered with either an acetate buffer (0.02M) or a citrate buffer (0.02M) and adjusted to pH 5.3. The 184 ml headspace of each serum bottle was initially N2 and then filled to an overpressure of 30 psi with either 95% CO, 5% CO2, or 70% CO, 15% CO2, 14% N2, 1% H2. Each bottle was inoculated with 2 ml of a *Clostridium autoethanogenum* culture. A shaking incubator was used and the reaction temperature was maintained at 37° C.

Once again, it is clear that 2,3-butanediol is produced irrespective of the buffer used in the experiment. Furthermore, it should also be noted that since the serum bottles were not pH controlled, the product also appeared to be produced with limited (or no) control of pH.

TABLE 5

Examples of 2,3-butanediol production in a variety of media. The media of the serum bottles were analysed after the active growth, i.e., the increase in cell mass levelled out after several days (4 to 7 days). Results are given in g/L.

| Media used and system | Final Acetate | Final Ethanol | Final 2,3-Butanediol |
|---|---|---|---|
| Serum Bottle 0.02M acetate buffer | 5.597 | 1.1 | 0.43 |
| Serum Bottle 0.02M Citrate buffer | 6.547 | 0.364 | 0.16 |

Example 4

Batch Fermentation in CSTR

Approximately 1.3 L of solution A was transferred into a 2 L fermenter and sparged with nitrogen. Resazurin (1.35 mL of a 2 g/L solution) was added. $H_3PO_4$ (85% solution, 2.025 mL) was added and the pH adjusted to 5.3 using conc. $NH_4OH(aq)$. Chromium(II)chloride was added until the ORP of the solution decreased to approximately −150 mV. Sodium polysulfide (6.07 ml of a 4.3M solution) was added and the pH adjusted to 5.5 using concentrated HCl. The solution was sparged with N2 for 1 hour before the addition of metal sulfide solution 1 (150 ml) and Solution B (15 ml). The solution was sparged with N2 then CO containing gas (3% H2; 30% N2; 47% CO; 20% CO2), before inoculation with an actively growing *Clostridium autoethanogenum* culture at a level of approximately 5% (v/v). Gas flow rate was adjusted to ensure the microbial culture was not limited in CO in order to maintain a high specific CO uptake. Results of the fermentation are shown in Table 6.

TABLE 6

2,3-butanediol productivity in a batch culture at varying specific CO uptakes.

| Day | Average specific CO uptake (mmol/g/min) | Average 2,3-butanediol production rate |
|---|---|---|
| 1-3 | 0.8 | 1.5 g/L/day |
| 5-6 | 0.1 | 0.25 g/L/day |

Total 2,3-butanediol accumulation over 7.5 days was approx 7.5 g/L. It is recognised that 2,3-butanediol is produced at low levels at lower specific CO uptake rates. However, when the gas is supplied such that the CO uptake rate can be maintained over 0.4 mmol/g/min, 2,3-butanediol productivity increase significantly. In this instance, the specific CO uptake is maintained at an average of 0.8 mmol/g/min over several days and 1,3-butanediol is produced at a rate in excess of 1 g/L.

Example 5

Batch Fermentation in CSTR

Approximately 1.3 L of solution A was transferred into a 2 L fermenter and sparged with nitrogen. $H_3PO_4$ (85% solution, 2.025 mL, 30 mM) was added and the pH adjusted to 5.3 using concentrated $NH_4OH(aq)$. Solution B (13.5 ml) was added and the solution sparged with N2. Chromium(II)chloride was added until the ORP of the solution decreased to approximately −150 mV. Resazurin (1.35 mL of a 2 g/L solution) was added. Sodium polysulfide (2.85 ml of a 6M solution) was added and the solution sparged with N2 for 12 hours before switching to CO containing gas (1% H2; 14% N2; 70% CO; 15% CO2). The pH was adjusted to 5.5 with concentrated HCl before the addition of metal sulfide solution 1 (150 ml). The solution was sparged with the CO containing gas for a further 30 minutes before inoculation with an actively growing *Clostridium autoethanogenum* culture at a level of approximately 5% (v/v). Again, gas flow rate was adjusted to ensure the microbial culture was not limited in CO in order to maintain a high specific CO uptake. Results of the fermentation are shown in Table 7.

TABLE 7

2,3-butanediol productivity in a batch culture at varying specific CO uptakes.

| Day | Average CO uptake (mmol/g/min) | Average 2,3-butanediol production rate |
|---|---|---|
| 1-4 | 0.85 | 0.8 g/L/day |
| 5-6 | 0.3 | 0.25 g/L/day |

Total 2,3-butanediol after approx 6 days was 5 g/L. Once again, elevated specific CO uptake results in significantly higher 2,3-butanediol productivity of at least 0.5 g/L/day.

Example 6

Batch Fermentation in CSTR

Approximately 1.3 L of solution A was transferred into a 1.5 L fermenter and sparged with nitrogen. $H_3PO_4$ (85% solution, 2.25 mL) was added and the pH adjusted to 5.3 using concentrated $NH_4OH(aq)$. Solution B (15 ml) was added and the solution sparged with N2. Chromium(II)chloride was added until the ORP of the solution decreased to approximately −150 mV. Resazurin (1.5 mL of a 2 g/L solution) was added. Sodium polysulfide (1.5 ml of a 3M solution) was added and the solution sparged with N2 for 1 hour. 0.1M solutions of $FeCl_2$ (3.75 mL), $CoCl_2$ (1.875 mL), $NiCl_2$ (1.875 mL), $H_3BO_3$ (0.375 ml), $Na_2MoO_4$ (0.375 ml), $MnCl_2$ (0.375 ml), $Na_2WO_4$ (0.375 ml) and $ZnCl_2$ (0.1875 ml) were added and the solution sparged with CO containing gas (50% H2; 32% CO; 4% CO2; 32% CH4). The pH was adjusted to 5.5 with concentrated HCl before the addition of Solution C (150 ml). The solution was sparged with the CO containing gas for a further 30 minutes before inoculation with an actively growing *Clostridium autoethanogenum* culture at a level of approximately 5% (v/v). Gas flow rate was adjusted to ensure the microbial culture was not limited in CO in order to maintain a high specific CO uptake. Results of the fermentation are shown in Table 8.

TABLE 8

2,3-butanediol productivity in a batch culture at varying specific CO uptakes.

| Day | Average CO uptake (mmol/g/min) | Average 2,3-butanediol production rate |
|---|---|---|
| 0-4 | 0.07 | 0 |
| 5-14 | 0.15 | 0.2 g/L/day |

Total 2,3-butanediol concentration after 4 days was approximately 3 g/L. While the rates achieved are less than previous fermentations (examples 4 and 5), the substrate stream comprises a substantial portion of hydrogen. The results show that 2,3-butanediol is produced when using a mixed CO/H2 substrate.

Example 7

Continuous Fermentation in Continuous Stirred Tank Reactor

Media was prepared at pH 5.5 as follows. All ingredients in Solution D, with the exception of Cysteine-HCl were mixed in 400 ml distilled water. This solution was made anaerobic by heating to boiling and allowing it to cool to room temperature under a constant flow of 95% CO, 5% CO2 gas. Once cool, the Cysteine-HCl was added and the pH of the solution adjusted to 5.5 before making the volume up to 1000 ml; anaerobicity was maintained throughout the experiments.

A five-liter bioreactor was charged with 4.9 L of LM33 media prepared as described above. The gas was switched to CO containing gas (1% H2; 14% N2; 70% CO; 15% CO2) at atmospheric pressure prior to inoculation with 100 ml of a *Clostridium autoethanogenum* culture. The bioreactor was maintained at 37° C. stirred at 200 rpm at the start of the culture. During the growth phase, the agitation was increased to 400 rpm. The pH was adjusted to 5.5 and maintained by automatic addition of 5 M NaOH. Fresh anaerobic media was continuously added into the bioreactor to maintain a defined biomass and acetate level in the bioreactor. 2,3 butanediol productivity is highlighted in Table 9.

TABLE 9

2,3-butanediol productivity in a continuous culture.

| Day | Average CO uptake (mmol/g/min) | Average 2,3-butanediol production rate |
|---|---|---|
| 1-87 | 0.3 | <0.1 g/L/day |
| 90-92 | 0.6 | 1.2 g/L/day |
| 93-95 | 0.4 | 0.87 g/L/day |

During the first 89 days of continuous operation, the fermenter was operated under CO limited conditions and minimal 2,3-butanediol was produced. However, around day 88, gas flow was increased, such that specific CO uptake increased. At this stage, 2,3-butanediol productivity increased significantly to at least 1.2 g/L/day. Around day 92, the gas flow was reduced such that the specific uptake of the culture decreased to around 0.4 mmol/g/min and the 2,3-butanediol productivity also dropped. However, even at an average specific uptake of approximately 0.4 mmol/g/min, 2,3-butanediol productivity remained at least 0.5 g/L/day.

Example 8

Batch Fermentation in CSTR

Approximately 1.3 L of solution A was transferred into a 2 L fermenter and sparged with nitrogen. $H_3PO_4$ (85% solution, 1.5 ml) was added and the pH adjusted to 5.3 using conc. $NH_4OH(aq)$. Solution B (15 ml) was added and the solution sparged with N2. Chromium(II)chloride was added until the ORP of the solution decreased to approximately −150 mV. Sodium polysulfide (1 ml of a 3M solution) was added and the solution sparged with N2 for 12 hours. 0.1M solutions of $FeCl_2$ (3.75 mL), $CoCl_2$ (1.875 mL), $NiCl_2$ (1.875 mL), $H_3BO_3$ (0.375 ml), $Na_2MoO_4$ (0.375 ml), $MnCl_2$ (0.375 ml), $Na_2WO_4$ (0.375 ml) and $ZnCl_2$ (0.2 ml) were added and the solution sparged with CO containing gas (1% H2; 14% N2; 70% CO; 15% CO2).

Resazurin (1 mL of a 2 g/L solution) was added. The pH was adjusted to 5.5 with concentrated HCl and the solution was sparged with the CO containing gas for a further 30 minutes before inoculation with an actively growing *Clostridium autoethanogenum* culture at a level of approximately 5% (v/v). Table 10 shows the accumulated 2,3-butanediol product in a fermenter after approximately 2 weeks operation. The specific CO uptake rates have been corrected for the culture viability. Culture viability was determined using the methods described in WO2009/022925, which is incorporated herein by reference.

TABLE 10

2,3-butanediol accumulation after 14 days batch fermentation.

| Day | Specific CO uptake (mmol/g/min) | 2,3-butanediol (accumulated product) |
|---|---|---|
| 13 | 0.6 | 8.67 g/L |
| 14 | 0.5 | 9.27 g/L |

Over the 24 hour period from day 13-14, the specific CO uptake was maintained at approximately 0.5 mmol/g/min and 2,3-butanediol productivity was 0.6 g/L/day.

Example 9

Gene Regulation of 2,3-Butanediol Production in LZ1560

Samples were taken from three fermentations to determine gene expression during 2,3-butanediol production. One sample was taken from the batch fermentation described in Example 8 on day 13, wherein products including ethanol and 2,3-butanediol were being produced. The sample is designated R12 in the results hereinafter. The second sample was taken from a batch fermentation producing both ethanol and 2,3-butanediol. The sample is designated R11 in the results. The third sample (R2) was taken from the continuous fermentation operating under similar conditions as Example 7 on days 1-89. The microbial culture was CO limited and the fermentation broth had a stable acetate concentration of approximately 13 g/L, ethanol concentration of less than 1 g/L and insignificant amounts of 2,3-butanediol. Real-Time PCR was used to determine whether genes were upregulated or downregulated relative to R2.

RNA Extraction and cDNA Synthesis Procedure:

Total RNA was isolated from approximately $2.5 \times 10^9$ bacterial cells using Aurum Total RNA Fatty and Fibrous Tissue Kit (Biorad). On-column DNase was digested using the RNase-free DNase set (Biorad). Total RNA was quantified using spectrophotometer and its purity (measured by the $A_{260/280}$ ratio) was determined before cDNA synthesis using iScript Select cDNA synthesis kit (Biorad).

Real-Time PCR Procedure:

Primers for Real-Time PCR, were designed using the freeware Primer3 based on LanzaTech's proprietary in-house genome sequence. Real-Time PCR reaction mixtures containing 12.5 µL 2×SYBR Green PCR Master Mix (Biorad), 1.5 µL of each of 1 µM primer forward and reverse, 5 µL of 10× diluted cDNA template, and sterile water to a total volume of 25 µL were assembled. The mixtures were heated to 95° C. for 3 minutes, followed by 40 cycles of 95° C. for 15 seconds, 55° C. for 15 seconds and 72° C. for 30 seconds. For detection of primer dimerisation or other artifacts of amplification, a melting-curve analysis was performed immediately after completion of the real-time PCR (38 cycles of 58° C. to 95° C. at 1° C./seconds). All reactions were performed in triplicate. Quantification of gene expression was performed using a MyiQ Single Colour Real-Time PCR Detection System (Biorad) and real-time data were analyzed using the iQ5 optical system software (Biorad).

Results:

The raw Ct values, together with the relative gene expression and standard errors, generated from the Real-Time PCR assay are presented in Table 11. RNA polymerase beta chain (rpoB) was selected as reference gene for normalizing gene expression. Relative quantification using the Comparative $\Delta C_T$ method was used to calculate the relative gene expression of 2,3BDH. The acetate-producing culture (R2) was selected as calibrator (reference standard) in all analysis.

TABLE 11

Derivation of relative gene expression values from raw Ct data. Relative expressions were normalized by rpoB and calibrated using Reactor 2. SE = standard error of the mean. (Any relative expression above 1 shows up regulation)

| Genes | Reactor | Raw Ct | Mean Ct | SD Ct | Relative expression | Relative expression SE |
|---|---|---|---|---|---|---|
| rpoB | 11 | 36.36 | 35.4 | 0.846 | NA | NA |
| | 11 | 35.07 | | | | |
| | 11 | 34.77 | | | | |
| | 12 | 32.47 | 32.7 | 0.258 | NA | NA |
| | 12 | 32.65 | | | | |
| | 12 | 32.98 | | | | |
| | 2 | 31.76 | 31.76 | 0.051 | NA | NA |
| | 2 | 31.81 | | | | |
| | 2 | 31.71 | | | | |
| 2,3BDH | 11 | 27.01 | 26.57 | 0.422 | 4.75 | 1.8 |
| | 11 | 26.53 | | | | |
| | 11 | 26.17 | | | | |
| | 12 | 23.23 | 23.18 | 0.038 | 7.64 | 0.8 |
| | 12 | 23.15 | | | | |
| | 12 | 23.17 | | | | |
| | 2 | 24.81 | 25.18 | 0.559 | 1 | 0.23 |
| | 2 | 24.91 | | | | |
| | 2 | 25.82 | | | | |

Real-time PCR data presented in this study shows that 2,3-butanediol gene expression is significantly higher in solventogenic cultures (R11/R12) compared to acetogenic cultures (R2). The microbial culture of R12, which was producing approximately 0.6 g/L/day 2,3-butanediol at the time of cell harvest, shows the highest gene up-regulation (7.64±0.8 fold), relative to R2. This is followed by R11 with 4.75±1.8 fold up-regulation of the gene, which had a total 2,3-butanediol production of 1.53 g/L, when the cells were harvested.

Figure 1:
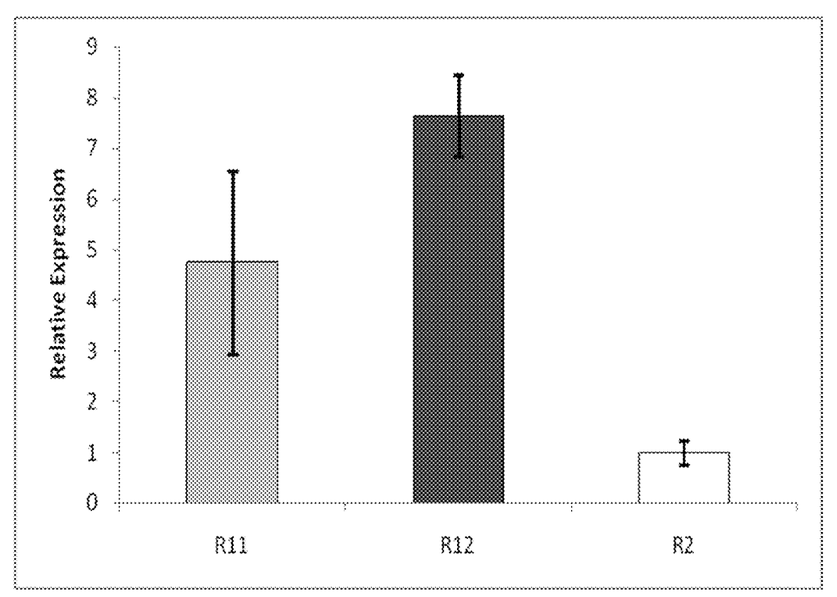
The FIGURE shows relative gene expression of 2,3-butanediol dehydrogenase (2,3BDH) in three fermenters.

The FIGURE shows relative gene expression of 2,3-butanediol dehydrogenase (2,3BDH) in three fermenters (R11, R12 and R2). Acetate-producing R2 is selected as calibrator and gene expression was normalized using rpoB as reference gene. Error bar=standard error of mean. N=3. Clearly, 2,3-butanediol dehydrogenase is upregulated in microbial cultures that produce 2,3-butanediol. The microbial culture in R2 has a specific CO uptake of approximately 0.3 mmol/g/min, whereas the culture in R12 has a specific uptake of approximately 0.6 mmol/g/min. Increasing the amount of CO provided to the culture results in an increase in CO uptake and a subsequent increase in 2,3-butanediol dehydrogenase gene expression. The increase in 2,3-butanediol dehydrogenase gene expression results in an increase in overall 2,3-butanediol productivity.

Example 10: Comparative Example

Two experiments were conducted to reproduce the experiments reported by Abrini et at (*Clostridium autoethanogenum*, sp. November, An Anaerobic Bacterium That Produces Ethanol From Carbon Monoxide; *Arch. Microbiol.*, 161: 345-351 (1994)). The two experiments were conducted because it was difficult to achieve the exact amount of substrate reported by Abrini et al.

Example 10A

*Clostridium autoethanogenum* DSM-10061 was maintained in PETC-MES media in the presence of 5 g/l fructose and 30 psi of mill gas (52% CO, 32% $N_2$, 13% $CO_2$, 3% $H_2$) for routine cultivations. For growth experiments, technical triplicates of 250 ml capacity serum bottles with 50 ml PETC-MES media (Table 12) were inoculated with 1 ml of 2.5 day old culture. Following inoculation, the headspace of the serum bottles was exchanged with 30 psi of 35.2% CO, 35.1% $CO_2$, and 29.7% $N_2$, was incubated at 37° C. with agitation for 221 hours. Microbial growth was estimated by measuring optical density at 600 nm ($OD_{600}$) using spectrophotometer.

TABLE 12

| PETC media | |
|---|---|
| Media component | Concentration per 1.0 L of media |
| $NH_4Cl$ | 1 g |
| KCl | 0.1 g |
| $MgSO_4 \cdot 7H_2O$ | 0.2 g |
| NaCl | 0.8 g |
| $KH_2PO_4$ | 0.1 g |
| $CaCl_2$ | 0.02 g |
| Trace metal solution | 10 ml |
| Wolfe's vitamin solution | 10 ml |
| Yeast Extract | 1 g |
| Resazurin (2 g/L stock) | 0.5 ml |
| $NaHCO_3$ | 2 g |
| Reducing agent | 0.006-0.008% (v/v) |
| Distilled water | Up to 1 L, pH 5.5 (adjusted with HCl) |
| Wolfe's vitamin solution | per L of Stock |
| Biotin | 2 mg |
| Folic acid | 2 mg |
| Pyridoxine hydrochloride | 10 mg |
| Thiamine•HCl | 5 mg |
| Riboflavin | 5 mg |
| Nicotinic acid | 5 mg |
| Calcium D-(+)-pantothenate | 5 mg |
| Vitamin $B_{12}$ | 0.1 mg |
| p-Aminobenzoic acid | 5 mg |
| Thioctic acid | 5 mg |
| Distilled water | To 1 L |
| Trace metal solution | per L of stock |
| Nitrilotriacetic Acid | 2 g |
| $MnSO_4 \cdot H_2O$ | 1 g |
| Fe $(SO_4)_2(NH_4)_2 \cdot 6H_2O$ | 0.8 g |
| $CoCl_2 \cdot 6H_2O$ | 0.2 g |
| $ZnSO_4 \cdot 7H_2O$ | 0.2 mg |
| $CuCl_2 \cdot 2H_2O$ | 0.02 g |
| $NaMoO_4 \cdot 2H_2O$ | 0.02 g |
| $Na_2SeO_3$ | 0.02 g |
| $NiCl_2 \cdot 6H_2O$ | 0.02 g |

TABLE 12-continued

| PETC media | |
|---|---|
| Na$_2$WO$_4$•2H$_2$O | 0.02 g |
| Distilled water | To 1 L |
| Reducing agent stock | per 100 mL of stock |
| NaOH | 0.9 g |
| Cystein•HCl | 4 g |
| Na$_2$S | 4 g |
| Distilled water | To 100 ml |

Analysis of metabolites were performed by HPLC using an Agilent 1100 Series HPLC system equipped with a RID operated at 35° C. (Refractive Index Detector) and an Alltech IOA-2000 Organic acid column (150×6.5 mm, particle size 5 µm) kept at 60° C. Slightly acidified water was used (0.005 M H$_2$SO$_4$) as mobile phase with a flow rate of 0.7 ml/min. To remove proteins and other cell residues, 400 µl samples were mixed with 100 µl of a 2% (w/v) 5-Sulfosalicylic acid and centrifuged at 14,000×g for 3 min to separate precipitated residues. 10 µl of the supernatant were then injected into the HPLC for analyses.

Results

After an incubation period of 221 hours, 1 ml of liquid culture was harvested for OD$_{600}$ measurement and HPLC analysis, and the results are presented in Table 2. On average, *C. autoethanogenum* reached OD$_{600}$ of 0.153 and accumulated 2.65 g/l of acetate, 0.18 g/l ethanol and no 2,3-butanediol.

TABLE 2

OD$_{600}$ and metabolite profile of *C. autoethanogenum* under autotrophic conditions

| | OD600 | Acetate (g/l) | EtOH (g/l) | 2,3-BDO (g/l) |
|---|---|---|---|---|
| *C. auto* 1 | 0.180 | 2.70 | 0.17 | 0 |
| *C. auto* 2 | 0.124 | 2.49 | 0.16 | 0 |
| *C. auto* 3 | 0.155 | 2.75 | 0.21 | 0 |
| Average | 0.153 | 2.65 | 0.18 | 0 |
| Standard Error | 0.009 | 0.046 | 0.009 | 0 |

The results of this experiment show that the Abrini strain under the conditions similar to that reported by Abrini does not produce any 2,3-butanediol.

Example 10B

*Clostridium autoethanogenum* DSM-10061(Abrini strain) was maintained in PETC-MES media in the presence of 5 g/l fructose and 30 psi of steel mill gas (52% CO, 32% N2, 13% CO2, 3% H2) for routine cultivations. For growth experiments, technical duplicates of 250 ml capacity serum bottles with 50 ml PETC-MES media (Table 12 above) were inoculated with 1 ml of 2.5 day old culture. Following inoculation, the headspace of the serum bottles was exchanged with 30 psi of 68.2% CO, 3.9% CO2, and 27.9% N2, was incubated at 37° C. with agitation for 115 hours. Microbial growth was estimated by measuring optical density at 600 nm (OD$_{600}$) using spectrophotometer.

Analysis of metabolites were performed as in example 10A above.

Results

After incubation period of 115 hours, 1 ml of liquid culture was harvested for OD$_{600}$ measurement and HPLC analysis, and the results are presented in Table 2. On average, *C. autoethanogenum* reached OD$_{600}$ of 0.33 and accumulated 2.38 g/l of acetate, 1.05 g/l ethanol and no 2,3-butanediol.

TABLE 2

OD$_{600}$ and metabolite profile of *C. autoethanogenum* under autotrophic conditions

| | OD600 | Acetate (g/l) | EtOH (g/l) | 2,3-BDO (g/l) |
|---|---|---|---|---|
| *C. auto* 1 | 0.34 | 2.51 | 1.10 | 0 |
| *C. auto* 2 | 0.32 | 2.24 | 0.99 | 0 |
| Average | 0.33 | 2.38 | 1.05 | 0 |
| Standard Error | 0.01 | 0.10 | 0.04 | 0 |

The results of this experiment show that the Abrini strain does not produce any 2,3-butanediol under the conditions similar to those reported by Abrini et al. It is noted that at CO concentration slightly below and above those reported by Abrini no 2,3-butanediol is produced. It is also observed that increasing the CO concentration does not result in an increase in the production of acetate and ethanol. Comparing example 10A vs. 10B, it is observed that ethanol production increases while acetate production decreases.

The invention has been described herein with reference to certain preferred embodiments, in order to enable the reader to practice the invention without undue experimentation. Those skilled in the art will appreciate that the invention is susceptible to variations and modifications other than those specifically described. It is to be understood that the invention includes all such variations and modifications. Furthermore, titles, headings, or the like are provided to enhance the reader's comprehension of this document, and should not be read as limiting the scope of the present invention.

The entire disclosures of all applications, patents and publications, cited above and below, if any, are hereby incorporated by reference.

The reference to any prior art in this specification is not, and should not be taken as, an acknowledgment or any form of suggestion that that prior art forms part of the common general knowledge in the United States of America or any country in the world.

Throughout this specification and any claims which follow, unless the context requires otherwise, the words "comprise", "comprising" and the like, are to be construed in an inclusive sense as opposed to an exclusive sense, that is to say, in the sense of "including, but not limited to".

What we claim is:

1. A method of producing 2,3-butanediol by microbial fermentation of a gaseous substrate comprising CO, the method comprising:
   a. continuously providing the gaseous substrate to a bioreactor; and
   b. anaerobically fermenting the substrate in the bioreactor, the bioreactor comprising a culture of at least one acetogenic bacterium to produce 2,3-butanediol; wherein the gaseous substrate is provided such that a specific rate of CO uptake of at least 0.4 mmol CO/gram dry cells weight of bacteria/minute by the culture is maintained and 2,3-butanediol is produced at a productivity greater than 0.2 g/L/per day.

2. The method of claim 1 further comprising converting the 2,3-butanediol to a compound selected from the group consisting of butene(s), butadiene, methyl ethyl ketone (MEK) and mixtures thereof.

3. The method of claim 2 further comprising converting the butene(s), butadiene or methyl ethyl ketone to a chemical product.

4. The method of claim 3 where the methyl ethyl ketone is converted to 2-butanol.

5. The method according to claim 1, wherein the substrate is provided such that a specific uptake rate of at least 0.6 mmol CO/g/min is maintained.

6. The method according to claim 1, wherein the substrate is provided such that a specific uptake rate of at least 0.8 mmol CO/g/min is maintained.

7. The method according to claim 1, wherein the substrate is provided such that a specific uptake rate of at least 1.0 mmol CO/g/min is maintained.

8. The method according to claim 1, wherein the gaseous substrate comprises at least 15% to about 100% CO by volume.

9. The method according to claim 1, wherein the gaseous substrate comprises a gas obtained as a by-product from an industrial process.

10. The method according to claim 9, wherein the gaseous substrate comprises waste gas from a steel mill.

11. The method according to claim 1 wherein the acetogenic bacterium is *Clostridium autoethanogenum*.

12. The method according to claim 1 wherein ethanol is produced as a co-product of the fermentation.

13. The method according to claim 1 wherein the acetogenic bacterium is the *Clostridium autoethanogenum* strain deposited at the German Collection of Microorganisms and Cell Cultures (DSMZ) under the accession number DSM 19630.

14. A method of producing 2,3-butanediol by microbial fermentation of a gaseous substrate comprising CO, the method-comprising:
  a. continuously providing the gaseous substrate to a bioreactor;
  b. anaerobically fermenting the gaseous substrate in the bioreactor, the bioreactor comprising a culture of at least one acetogenic bacterium, wherein the at least one acetogenic bacterium comprises at least one 2,3-butanediol dehydrogenase gene;
  c. upregulating the 2,3-butanediol dehydrogenase gene by providing the gaseous substrate such that the specific uptake of CO by the at least one acetogenic bacterium is at least 0.4 mmol/g/min, and such that 2,3-butanediol is produced at a productivity greater than 0.2 g/L/per day; and
  d. converting the 2,3-butanediol produced in step (c) to a compound selected from the group consisting of butane, butadiene, methyl ethyl ketone and mixtures thereof.

15. The method according to claim 14 wherein the acetogenic bacterium comprises *Clostridium autoethanogenum*.

16. The method according to claim 15 wherein the acetogenic bacterium is the *Clostridium autoethanogenum* strain deposited at the German Collection of Microorganisms and Cell Cultures (DSMZ) under the accession number DSM 19630.

17. The method of claim 14 further comprising converting the butene(s), butadiene or methyl ethyl ketone to a chemical product.

18. The method according to claim 14, wherein the substrate is provided such that a specific uptake rate of at least 0.6 mmol CO/g/min is maintained.

19. The method according to claim 14, wherein the gaseous substrate comprises at least 15% to about 100% CO by volume.

20. The method according to claim 14, wherein the gaseous substrate comprises waste gas from a steel mill.

21. The method according to claim 14 wherein ethanol is produced as a co-product of the fermentation.

* * * * *